United States Patent [19]
Tripp et al.

[11] Patent Number: 5,789,194
[45] Date of Patent: Aug. 4, 1998

[54] PARASITIC HELMINTH VENOM ALLERGEN ANTIGEN 5-LIKE GENES AND PROTEINS

[75] Inventors: Cynthia Ann Tripp; Nancy Wisnewski, both of Ft. Collins, Colo.

[73] Assignee: Heska Corporation, Ft. Collins, Colo.

[21] Appl. No.: 450,944

[22] Filed: May 23, 1995

[51] Int. Cl.$^6$ .......................... C12P 21/00; C07H 21/04; C07K 1/00; A61K 39/00

[52] U.S. Cl. .................. 435/69.1; 435/69.1; 435/69.3; 435/252.3; 536/23.1; 536/23.4; 536/23.5; 530/350; 530/300; 530/387.1; 424/265.1; 424/151.1; 424/191.1; 424/130.1

[58] Field of Search ................ 424/265.1, 151.1, 424/191.1, 130.1; 435/69.1, 69.3, 252.3, 320.1; 530/350, 300, 387.1; 536/23.1, 23.7, 23.4, 23.5

[56] References Cited

FOREIGN PATENT DOCUMENTS

| WO 90/10230 A1 | 9/1990 | WIPO . |
|---|---|---|
| 9211379 | 9/1992 | WIPO . |
| WO 94/20623 | 9/1994 | WIPO . |

OTHER PUBLICATIONS

Facon et al. (1991) Mol. Biochem. Parasitol. 45, 233–240.
Chamekh et al (1992) J. Clin. Invest. 89, 458–464.
Brilliantes et al., 1994, Cell, 77:513–523.
Hotez et al., 1994, *J. Infectious Dis.*, 170:918–926.
Moyle et al, 1994, *J. Biological Chem.*, 269:10008–10015.
Chamekh et al., 1990, *J. Immunological Meth.*, 134:129–137.
Fang et al., 1988, *Proc. Natl. Acad. Sci. USA*, 85:895–899.
Lightowlers et al., 1989, *Mol. Biochem. Parasitol.*, 37:171–182.
Lu et al., 1993, *J. Immunol.*, 150:2823–2830.
Valdez et al., 1994, *J. Parasitol.* 80(6):931–936.

*Primary Examiner*—Paula K. Hutzell
*Assistant Examiner*—Khalid Masood
*Attorney, Agent, or Firm*—Sheridan Ross P.C.

[57] ABSTRACT

The present invention relates to parasitic helminth venom allergen antigen 5-like proteins; to parasitic helminth venom allergen antigen 5-like nucleic acid molecules, including those that encode such proteins; and to antibodies raised against such proteins. The present invention also includes methods to obtain such proteins, nucleic acid molecules and antibodies. Also included in the present invention are therapeutic compositions comprising such proteins, nucleic acid molecules and/or antibodies, as well as the use of such therapeutic compositions to protect animals from diseases caused by parasitic helminths.

13 Claims, No Drawings

5,789,194

1

PARASITIC HELMINTH VENOM ALLERGEN ANTIGEN 5-LIKE GENES AND PROTEINS

FIELD OF THE INVENTION

The present invention relates to parasitic helminth venom allergen antigen 5-like proteins, nucleic acid molecules having sequences that encode such proteins, and antibodies raised against such proteins. The present invention also includes therapeutic compositions comprising such nucleic acid molecules, proteins and antibodies, as well as their use to protect animals from diseases caused by parasitic helminths, such as heartworm or onchocerciasis.

BACKGROUND OF THE INVENTION

Parasitic helminth infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasitic helminth infections, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

It is particularly difficult to develop vaccines against parasitic helminth infections both because of the complexity of the parasite's life cycle and because, while administration of parasites or parasite antigens can lead to the production of a significant antibody response, the immune response is typically not sufficient to protect the animal against infection.

As an example of the complexity of parasitic helminths, the life cycle of *D. immitis*, the helminth that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system of the dog. One method of demonstrating infection in the dog is to detect the circulating microfilariae.

If the dog is maintained in an insect-free environment, the life cycle of the parasite cannot progress. However, when microfilariae are ingested by the female mosquito during blood feeding on an infected dog, subsequent development of the microfilariae into larvae occurs in the mosquito. The microfilariae go through two larval stages (L1 and L2) and finally become mature third stage larvae (L3) which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of the adult heartworms can be determined through thoracic examination.

2

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic helminthic infections are also widespread, and all require better treatment, including a preventative vaccine program. *O. volvulus*, for example, causes onchocerciasis (also known as river blindness) in humans. Up to 50 million people throughout the world are reported to be infected with *O. volvulus*, with over a million being blinded due to infection.

Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, including in Dirofilaria and Onchocerca, there is yet to be an effective vaccine developed for any parasitic helminth.

As such, there remains a need to identify an efficacious composition that protects animals against diseases caused by parasitic helminths and that, preferably, also protects animals from infection by such helminths.

SUMMARY OF THE INVENTION

The present invention relates to parasitic helminth venom allergen antigen 5-like proteins (parasitic helminth VA5 proteins); to parasitic helminth venom allergen antigen 5-like nucleic acid molecules (parasitic helminth VA5 nucleic acid molecules), including those that encode such proteins; and to antibodies raised against such proteins (anti-parasitic helminth VA5 antibodies). The present invention also includes methods to obtain such proteins, nucleic acid molecules and antibodies. Also included in the present invention are therapeutic compositions comprising such proteins, nucleic acid molecules and/or antibodies, as well as use of such therapeutic compositions to protect animals from diseases caused by parasitic helminths.

One embodiment of the present invention is an isolated parasitic helminth nucleic acid molecule that hybridizes under stringent hybridization conditions with a gene selected from the group consisting of a *Dirofilaria immitis* venom allergen antigen 5-like gene (i.e., a *D. immitis* VA5 gene) and an *Onchocerca volvulus* venom allergen antigen 5-like gene (i.e., an *O. volvulus* VA5 gene). A *D. immitis* VA5 gene preferably includes nucleic acid SEQ ID NO:1, and an *O. volvulus* VA5 gene preferably includes nucleic acid sequence SEQ ID NO:6. A VA5 nucleic acid molecule of the present invention can include a regulatory region of a parasitic helminth VA5 gene and/or can encode a parasitic helminth VA5 protein. Particularly preferred VA5 nucleic acid molecules include nucleic acid sequence SEQ ID NO:1, nucleic acid sequence SEQ ID NO:3, nucleic acid sequence SEQ ID NO:4, nucleic acid sequence SEQ ID NO:6 and/or nucleic acid sequence SEQ ID NO:8, as well as allelic variants of one or more of those nucleic acid molecules.

The present invention also relates to recombinant molecules, recombinant viruses and recombinant cells that include parasitic helminth VA5 nucleic acid molecules of the present invention. Also included are methods to produce such nucleic acid molecules, recombinant molecules, recombinant viruses and recombinant cells.

Another embodiment of the present invention includes a parasitic helminth venom allergen antigen 5-like protein (i.e., a parasitic helminth VA5 protein) or a protein that includes a parasitic helminth VA5 protein. A preferred parasitic helminth VA5 protein, when administered to an animal, is capable of eliciting an immune response against a natural parasitic helminth VA5 protein. Particularly preferred VA5 proteins are proteins that include amino acid sequence SEQ ID NO:2, amino acid sequence SEQ ID NO:5 and/or amino acid sequence SEQ ID NO:7, as well as proteins that are encoded by nucleic acid molecules that are allelic variants of the nucleic acid molecules that encode proteins having SEQ ID NO:2, SEQ ID NO:5, and/or SEQ ID:7.

The present invention also relates to mimetopes of parasitic helminth VA5 proteins as well as to isolated antibodies that selectively bind to parasitic helminth VA5 proteins or mimetopes thereof. Also included are methods, including recombinant methods, to produce proteins, mimetopes and antibodies of the present invention.

Yet another embodiment of the present invention is a therapeutic composition that is capable of protecting an animal from disease caused by a parasitic helminth. Such a therapeutic composition includes one or more of the following protective compounds: an isolated parasitic helminth venom allergen antigen 5-like protein or a mimetope thereof; an isolated parasitic helminth nucleic acid molecule that hybridizes under stringent hybridization conditions with a D. immitis VA5 gene and/or an O. volvulus VA5 gene; and an isolated antibody that selectively binds to a parasitic helminth venom allergen antigen 5-like protein. A preferred therapeutic composition of the present invention also includes an excipient, an adjuvant and/or a carrier. Preferred VA5 nucleic acid molecule compounds of the present invention include naked nucleic acid vaccines, recombinant virus vaccines and recombinant cell vaccines. Also included in the present invention is a method to protect an animal from disease caused by a parasitic helminth. The method includes the step of administering to the animal a therapeutic composition of the present invention.

Suitable parasitic helminths to use in the production (e.g., recombinant, natural, or synthetic production) of nucleic acid molecules, proteins and antibodies of the present invention include nematodes, cestodes and trematodes, with nematodes (such as filariid, ascarid, strongyle and trichostrongyle nematodes) being preferred, with filariids being more preferred, and with D. immitis and O. volvulus being even more preferred.

Suitable and preferred parasitic helminths from which to protect animals are as disclosed for use in the production of nucleic acid molecules, proteins and antibodies of the present invention. As such, preferred diseases from which to protect animals include diseases caused by nematodes, cestodes and/or trematodes, with diseases caused by nematodes being more preferred targets, and with diseases caused by filariids being even more preferred targets. Particularly preferred diseases from which to protect animals include heartworm and onchocerciasis.

DETAILED DESCRIPTION OF THE INVENTION

The present invention includes the surprising discovery that parasitic helminths produce a venom allergen antigen 5-like protein that, although reported for hymenopteran insects (see, for example, PCT International Publication No. WO 94/20623, by King, published Sep. 15, 1994, and references therein), has not been reported for parasitic helminths. This parasitic helminth protein, also referred to herein as a parasitic helminth venom allergen, as VA and as VA5, has utility in that it represents a novel target for anti-parasite vaccines and drugs. Without being bound by theory, it is believed that a parasitic helminth venom allergen may be involved in biasing the host immune response to a target that is not detrimental to the helminth and/or in otherwise abrogating, or at least reducing, host responses to parasitic helminth infection by, for example, altering cytokine, complement and/or other immune response activities. Venom allergen proteins may also be involved in reproduction, parasite tissue migration and tissue necrosis and may function as allergens per se. Although allergic responses are not usually observed in association with parasitic helminth infection, there are several suggestions of the existence of an allergic response in such infections. For example, reaction to dirofilariasis can include an IgE-based immune response, and infection with Onchocerca can be accompanied by a skin reaction. Parasitic helminth VA5 proteins of the present invention also share limited amino acid sequence homology with hookworm Ancylostoma caninum neutrophil inhibitory factor (about 13%) and with Mexican beaded lizard helothermine (about 27%), which blocks ryanodine receptors, thereby supporting a role for VA5 proteins of the present invention in immunosuppression, reduction of inflammation and in possible inhibition of other signal-trafficking activities associated with ryanodine receptors, such as fertilization, neurotransmitter release, T cell activation, hormone activation, proliferation, and muscle activity. Neutrophil inhibitory factor and ryanodine receptor activities are described, in, for example: Moyle et al., 1994, J. Biol. Chem. 269, 10008–10015; and Brillantes et al., 1994, Cell 77, 513–523.

The present invention includes not only parasitic helminth venom allergen proteins but also parasitic helminth venom allergen nucleic acid molecules and antibodies directed against parasitic helminth venom allergen proteins. Also included is the use of these proteins, nucleic acid molecules and antibodies as therapeutic compositions to treat parasitic helminth diseases as well as in other applications, such as those disclosed below.

One embodiment of the present invention is an isolated parasitic helminth venom allergen antigen 5-like protein. According to the present invention, an isolated, or biologically pure, protein, is a protein that has been removed from its natural milieu. As such, "isolated" and "biologically pure" do not necessarily reflect the extent to which the protein has been purified. An isolated VA5 protein of the present invention can be obtained from its natural source, can be produced using recombinant DNA technology or can be produced by chemical synthesis. As used herein, an isolated parasitic helminth VA5 protein can be a full-length protein or any homologue of such a protein. Examples of VA5 homologues include VA5 proteins in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue includes at least one epitope capable of eliciting an immune response against a parasitic helminth VA5 protein. That is, when the homologue is administered to an animal as an immunogen, using techniques known to those skilled in the art, the animal will produce a humoral and/or cellular immune response against at least one epitope of a parasitic helminth VA5 protein. The ability of a protein to effect an immune response, can be measured using techniques known to those skilled in the art.

Parasitic helminth VA5 protein homologues can be the result of natural allelic variation or natural mutation. VA5 protein homologues of the present invention can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to elicit an immune response against parasitic helminth VA5 proteins.

Parasitic helminth VA5 proteins of the present invention, including homologues of the full-length protein, have the further characteristic of being encoded by nucleic acid molecules that hybridize under stringent hybridization conditions to at least one of the following genes: (a) a gene encoding a *Dirofilaria immitis* venom allergen antigen 5-like protein (i.e., a *D. immitis* VA5 gene); and (b) a gene encoding an *Onchocerca volvulus* venom allergen antigen 5-like protein (i.e., an *O. volvulus* VA5 gene. It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., 1989, *Molecular Cloning: A Laboratory Manual*, Cold Spring Harbor Labs Press. Examples of such conditions are provided in the Examples section of the present application.

As used herein, a *D. immitis* VA5 gene includes all nucleic acid sequences related to a natural *D. immitis* VA5 gene such as regulatory regions that control production of the *D. immitis* VA5 protein encoded by that gene (such as, but not limited to, transcription, translation or post-translation control regions) as well as the coding region itself. In one embodiment, a *D. immitis* VA5 gene includes the nucleic acid sequence SEQ ID NO:1. Nucleic acid sequence SEQ ID NO:1 represents the deduced sequence of a CDNA (complementary DNA) nucleic acid molecule denoted herein as nDiVA$_{833}$, the production of which is disclosed in the Examples. It should be noted that since nucleic acid sequencing technology is not entirely error-free, SEQ ID NO:1 (as well as other nucleic acid and protein sequences presented herein), at best, represents an apparent nucleic acid sequence of the nucleic acid molecule encoding a *D. immitis* VA5 protein of the present invention.

In another embodiment, a *D. immitis* VA5 gene can be an allelic variant that includes a similar but not identical sequence to SEQ ID NO:1. An allelic variant of a *D. immitis* VA5 gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants are well known to those skilled in the art and would be expected to be found within a given parasitic helminth since the genome is diploid and/or among a group of two or more parasitic helminths.

Similarly, an *O. volvulus* VA5 gene includes all nucleic acid sequences related to a natural *O. volvulus* VA5 gene such as regulatory regions that control production of the *O. volvulus* VA5 protein encoded by that gene as well as the coding region itself. In one embodiment, an *O. volvulus* VA5 gene includes the nucleic acid sequence SEQ ID NO:6. Nucleic acid sequence SEQ ID NO:6 represents the deduced sequence of a cDNA (complementary DNA) nucleic acid molecule denoted herein as nOvVA$_{330}$, the production of which is disclosed in the Examples. In another embodiment, an *O. volvulus* VA5 gene can be an allelic variant that includes a similar but not identical sequence to SEQ ID NO:6.

The minimal size of a VA5 protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich.

As such, the minimal size of a nucleic acid molecule used to encode a VA5 protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a VA5 protein homologue of the present invention is from about 4 to about 6 amino acids in length, with preferred sizes depending on whether a full-length, fusion, multivalent, or functional portions of such proteins are desired.

Protein homologues of the present invention preferably are capable of eliciting an immune response against a parasitic helminth VA5 protein. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

Any parasitic helminth VA5 protein is a suitable protein of the present invention. Suitable parasitic helminths from which to isolate VA5 proteins (including isolation of the natural protein or production of the protein by recombinant or synthetic techniques) include nematodes, cestodes, and trematodes, with nematodes being preferred. Preferred nematodes from which to isolate VA5 proteins include filariid, ascarid, strongyle and trichostrongyle nematodes. Particularly preferred nematodes are those of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred nematodes include parasitic helminths of the genera Capillaria, Chabertia, Cooperia, Enterobius, Haemonchus, Nematodirus, oesophagostomum, ostertagia, Trichostrongylus and Trichuris. Preferred filariid nematodes include Dirofilaria, Onchocerca, Acanthocheilonema, Brugia, Dipetalonema, Loa, Parafilaria, Setaria, Stephanofilaria and Wuchereria filariid nematodes. Particularly preferred parasitic helminths are nematodes of the genera Dirofilaria and Onchocerca, with *D. immitis*, the parasite that causes heartworm, and *O. volvulus*, the parasite that causes onchocerciasis, being even more preferred.

A preferred parasitic helminth VA5 protein of the present invention is a compound that when administered to an animal in an effective manner, is capable of protecting that animal from disease caused by a parasitic helminth. As such, the parasitic helminth is essentially incapable of causing disease in an animal that is immunized with a parasitic helminth VA5 protein of the present invention. In accordance with the present invention, the ability of a VA5 protein of the present invention to protect an animal from disease by a parasitic helminth refers to the ability of that protein to treat, ameliorate and/or prevent disease, including infection leading to disease, caused by the parasitic helminth, preferably by eliciting an immune response against the parasitic helminth. Such an immune response can include humoral and/or cellular immune responses.

Suitable parasites to target include any parasite that is essentially incapable of causing disease in an animal administered a VA5 protein of the present invention. As such, a parasite to target includes any parasite that produces a protein having one or more epitopes that can be targeted by a humoral and/or cellular immune response against a VA5 protein of the present invention and/or that can be targeted by a compound that otherwise inhibits VA5 activity, thereby resulting in the reduced ability of the parasite to cause disease in an animal. Suitable and preferred parasites to target include those parasitic helminths disclosed above as being useful in the production of parasitic helminth proteins of the present invention.

It is to be appreciated that the present invention also includes mimetopes of VA5 proteins of the present invention that can be used in accordance with methods as disclosed for VA5 proteins of the present invention. As used herein, a mimetope of a VA5 protein of the present invention refers to any compound that is able to mimic the activity of such a VA5 protein, often because the mimetope has a structure that mimics the VA5 protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion protein that includes a parasitic helminth VA5 protein-containing domain attached to a fusion segment. Inclusion of a fusion segment as part of a VA5 protein of the present invention can enhance the protein's stability during production, storage and/or use. Depending on the segment's characteristics, a fusion segment can also act as an immunopotentiator to enhance the immune response mounted by an animal immunized with a parasitic helminth VA5 protein containing such a fusion segment. Furthermore, a fusion segment can function as a tool to simplify purification of a parasitic helminth VA5 protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the VA5-containing domain of the protein. Linkages between fusion segments and VA5-containing domains of fusion proteins can be susceptible to cleavage in order to enable straight-forward recovery of the VA5-containing domains of such proteins. Fusion proteins are preferably produced by culturing a recombinant cell transformed with a fusion nucleic acid molecule that encodes a protein including the fusion segment attached to either the carboxyl and/or amino terminal end of a VA5-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. An example of a particularly preferred fusion protein of the present invention is PHIS-PDiVA$_{205}$, production of which is disclosed herein.

Another embodiment of the present invention is a parasitic helminth VA5 protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a VA5 protein of the present invention attached to one or more compounds protective against one or more other infectious agents, particularly an agent that infects humans, cats, dogs, cattle and/or horses, such as, but not limited to: viruses (e.g., caliciviruses, distemper viruses, hepatitis viruses, herpesviruses, immunodeficiency viruses, infectious peritonitis viruses, leukemia viruses, panleukopenia viruses, parvoviruses, rabies viruses, other cancercausing or cancer-related viruses); bacteria (e.g., Leptospira, Rochalimaea); fungi and fungal-related microorganisms (e.g., Candida, Cryptococcus, Histoplasma); and other parasites (e.g., Babesia, Cryptosporidium, Eimeria, Encephalitozoon, Hepatozoon, Isospora, Microsporidia, Neospora, Nosema, Plasmodium, Pneumocystis, Toxoplasma, as well as helminth parasites, such as those disclosed herein). In one embodiment, a D. immitis VA5 protein of the present invention is attached to one or more additional compounds protective against heartworm. In another embodiment, an O. volvulus VA5 protein of the present invention is attached to one or more additional compounds protective against onchocerciasis.

A preferred parasitic helminth VA5 protein of the present invention is a protein encoded by a nucleic acid molecule that hybridizes under stringent hybridization conditions with nucleic acid molecule nDiVA$_{833}$ and/or nucleic acid molecule nOvVA$_{330}$. Such a VA5 protein is encoded by a nucleic acid molecule that hybridizes under stringent hybridization conditions with a nucleic acid molecule having nucleic acid sequence SEQ ID NO:1 and/or a nucleic acid molecule having nucleic acid sequence SEQ ID NO:6.

Translation of SEQ ID NO:1 suggests that nucleic acid molecule nDiVA$_{833}$ encodes a full-length D. immitis VA5 protein of about 221 amino acids, referred to herein as PDiVA$_{221}$, assuming an open reading frame having an initiation (start) codon spanning from about nucleotide 54 through about nucleotide 56 of SEQ ID NO:1 and a termination (stop) codon spanning from about nucleotide 717 through about nucleotide 719 of SEQ ID NO:1. This open reading frame, excluding the stop codon comprises nucleic acid molecule nDiVA$_{663}$ of the present invention, the nucleic acid sequence of which is represented herein by SEQ ID NO:3. It is to be noted that the open frame of nDiVA$_{833}$ extends an additional 9 nucleotides upstream from the first ATG codon, upstream of which is the stop codon TAA.

The deduced amino acid sequence of PDiVA$_{221}$ is represented herein as SEQ ID NO:2. Analysis of SEQ ID NO:2 suggests that PDiVA$_{221}$ includes a potential amino terminal signal peptide through about amino acid 16 of SEQ ID NO:2. As such, the present invention also includes a proposed mature (i.e., processed) protein denoted PDiVA$_{205}$, represented by amino acid sequence SEQ ID NO:5, which is encoded by nucleic acid molecule nDiVA$_{615}$, the nucleic acid sequence of which is represented herein as SEQ ID NO:4. PDiVA$_{205}$ has a calculated molecular weight of about 23.5 kilodaltons (kD) and an estimated pI of 9.75.

Comparison of amino acid sequence SEQ ID NO:2 (i.e., amino acid sequence of PDiVA$_{221}$) with amino acid sequences reported in GenBank indicates that SEQ ID NO:2 shares the following percent identities with the amino acid sequences of the following hymenopteran insect proteins: about 25% identical to fire ant venom allergen III (Acc. No. P35788); about 24% identical to white fact hornet venom allergen 5-3 (Acc. No. P10737); and about 24% identical to European hornet venom allergen 5-2 (Acc. No. P35782). SEQ ID NO:2 also shares about 27% identity with Mexican beaded lizard helothermine (Acc. No. U13619), about 27% identity with human testis-specific protein TPX-1 precursor (Acc. No. P16562), about 26% identity with mouse testis-specific protein TPX-1 precursor (Acc No. P16563), about 13% identity with hookworm Ancylostoma caninum neutrophil inhibitory factor precursor (Acc. No. A54419), and about 24% identity with mouse sperm-coating glycoprotein 1 precursor (Acc. No. Q03401).

Translation of SEQ ID NO:6 suggests that nucleic acid molecule nOvVA$_{330}$ encodes about 72 amino acids of the carboxyl terminal portion of O. volvulus VA5 protein, which is referred to herein as POvVA$_{72}$, assuming an open reading frame having a termination codon spanning from about nucleotide 217 through about nucleotide 219 of SEQ ID NO:6. The deduced amino acid sequence of POvVA$_{72}$ is represented herein as SEQ ID NO:7. Comparison of amino acid sequence SEQ ID NO:7 with amino acid sequences reported in GenBank indicates that SEQ ID NO:7 is about 42% identical over a region of about 48 amino acids to the amino acid sequence of the Dolichovespula maculata (white-face hornet) venom allergen 5 protein, about 40% identical over a region of about 48 amino acids to the amino acid sequences of the Vespa crabro (European hornet) and Dolichovespula arenaria (yellow hornet) venom allergen 5 proteins, about 37% identical over a region of about 49 amino acids to the amino acid sequence of the Solenopsis invicta (red imported fire ant) venom allergen 5 protein, and about 33% identical over a region of about 48 amino acids to the amino acid sequence of the Vespula vulgaris (yellow jacket) venom allergen 5 protein. It is also to be noted that the amino acid sequence of O. volvulus VA5 protein POvVA$_{72}$ is about 64% identical to the corresponding region (i.e. the carboxyl terminal 72 amino acids) of D. immitis VA5 protein PDiVA$_{221}$.

Preferred parasitic helminth VA proteins of the present invention include: proteins comprising amino acid sequences that are at least about 30%, preferably at least about 50%, more preferably at least about 75% and even more preferably at least about 90% identical to amino acid sequence SEQ ID NO:2; and proteins comprising an amino acid sequences that are at least about 45%, more preferably at least about 60%, even more preferably at least about 75% and even more preferably at least about 90% identical to amino acid sequence SEQ ID NO:7. More preferred parasitic helminth VA5 proteins of the present invention include: proteins encoded by at least a portion of SEQ ID NO:1 and, as such, have amino acid sequences that include at least a portion of SEQ ID NO:2; and proteins encoded by at least a portion of SEQ ID NO:6 and, as such, have amino acid sequences that include at least a portion of SEQ ID NO:7.

Particularly preferred parasitic helminth proteins of the present invention are proteins that include SEQ ID NO:2, SEQ ID NO:5, and/or SEQ ID NO:7 (including, but not limited to the encoded proteins, full-length proteins, processed proteins, fusion proteins and multivalent proteins) as well as proteins that are truncated homologues of proteins that include SEQ ID NO:2, SEQ ID NO:5, and/or SEQ ID NO:7. Even more preferred proteins include PDiVA$_{221}$, PDiVA$_{205}$, PDiVA$_{224}$, PHIS-PDiVA$_{205}$, and POvVA$_{72}$. Examples of methods to produce such proteins are disclosed herein, including in the Examples section.

Another embodiment of the present invention is an isolated parasitic helminth nucleic acid molecule that hybridizes under stringent hybridization conditions with a gene selected from the group consisting of a D. immitisvenom allergen antigen 5-like gene and an O. volvulus venom allergen antigen 5-like gene. The identifying characteristics of such genes are heretofore described. A nucleic acid molecule of the present invention can include an isolated natural parasitic helminth VA5 gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions. Suitable and preferred parasitic helminths are disclosed above.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated parasitic helminth VA5 nucleic acid molecule of the present invention can be obtained from its natural source either as an entire (i.e., complete) gene or a portion thereof capable of forming a stable hybrid with that gene. An isolated parasitic helminth VA5 nucleic acid molecule can also be produced using recombinant DNA technology (e.g., polymerase chain reaction (PCR) amplification, cloning) or chemical synthesis. Isolated parasitic helminth VA5 nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a parasitic helminth VA5 protein of the present invention or to form stable hybrids under stringent conditions with natural gene isolates.

A parasitic helminth VA5 nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of a parasitic helminth VA5 protein) and/or by hybridization with a $D.$ $immitis$ VA5 gene and/or with an $O.$ $volvulus$ VA5 gene.

An isolated nucleic acid molecule of the present invention can include a nucleic acid sequence that encodes at least one parasitic helminth VA5 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth VA5 protein. As heretofore disclosed, parasitic helminth VA5 proteins of the present invention include, but are not limited to, proteins having full-length parasitic helminth VA5 coding regions, proteins having partial parasitic helminth VA5 coding regions, fusion proteins, multivalent protective proteins and combinations thereof.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal by direct injection (i.e. as a naked nucleic acid) or in a vehicle such as a recombinant virus vaccine or a recombinant cell vaccine.

One embodiment of the present invention is a parasitic helminth VA5 nucleic acid molecule that hybridizes under stringent hybridization conditions with nucleic acid molecule $nDiVA_{833}$ and/or nucleic acid molecule $nOvVA_{330}$. Such parasitic helminth nucleic acid molecules can hybridize under stringent hybridization conditions with a nucleic acid molecule having nucleic acid sequence SEQ ID NO:1 and/or with a nucleic acid molecule having nucleic acid sequence SEQ ID NO:6.

The deduced nucleic acid sequence of $nDiVA_{833}$ is represented herein as SEQ ID NO:1; and the nucleic acid sequence of $nDiVA_{663}$, which contains the open reading frame of $nDiVA_{833}$ without the stop codon, is represented herein as SEQ ID NO:3. The deduced nucleic acid sequence of $nOvVA_{330}$ is represented herein as SEQ ID NO:6; and the nucleic acid sequence of $nOvVA_{216}$, which contains the open reading frame of $nDiVA_{330}$ without the stop codon, is represented herein as SEQ ID NO:8. Comparison of SEQ ID NO:3 with nucleic acid sequences reported in GenBank indicates that SEQ ID NO:3 is about 51% identical to the Vespula vulgaris (yellow jacket) venom allergen 5 gene, and about 46% identical to the $Dolichovespula$ $maculata$ (whiteface hornet) venom allergen 5 gene. Comparison of SEQ ID NO:8 with nucleic acid sequences reported in GenBank indicates that SEQ ID NO:8 is about 56% identical to the $Vespula$ $vulgaris$ (yellow jacket) venom allergen 5 gene, and about 61% identical to the $Dolichovespula$ $maculata$ (whiteface hornet) venom allergen 5 gene. It is also to be noted that the nucleic acid sequence of the coding region of $O.$ $volvulus$ VA5 nucleic acid molecule $nOvVA_{330}$ (i.e., $nOvVA_{216}$) is about 77% identical to the corresponding region (i.e. the carboxyl terminal 216 nucleotide coding region) of $D.$ $immitis$ VA5 nucleic acid molecule $nDiVA_{833}$. About 72% identity is found between $nOvVA_{330}$ (i.e., the coding region and 3' untranslated region) and the corresponding region of $nDiVA_{833}$.

Preferred parasitic helminth nucleic acid molecules include nucleic acid molecules having a nucleic acid sequence that is at least about 55%, preferably at least about 70%, more preferably at least about 80%, and even more preferably at least about 90% identical to nucleic acid sequence SEQ ID NO:3 and nucleic acid molecules having a nucleic acid sequence that is at least about 65%, preferably at least about 75%, more preferably at least about 85%, and even more preferably at least about 90% identical to nucleic acid sequence SEQ ID NO:8.

A preferred nucleic acid molecule of the present invention includes at least a portion of nucleic acid sequence SEQ ID NO:1 or SEQ ID NO:6 that is capable of hybridizing to a $D.$ $immitis$ VA5 gene and/or to a $O.$ $volvulus$ VA5 gene of the present invention. More preferred is a nucleic acid molecule that includes nucleic acid sequence SEQ ID NO:1, nucleic acid sequence SEQ ID NO:3, nucleic acid sequence SEQ ID NO:4, nucleic acid sequence SEQ ID NO:6, and/or nucleic acid sequence SEQ ID NO:8. Such a nucleic acid molecule can include nucleotides in addition to those included in the SEQ ID NOs, such as, but not limited to, a full-length gene, a full-length coding region (particularly in the case of SEQ ID NO:6 and SEQ ID NO:8), a nucleic acid molecule encoding a fusion protein, or a nucleic acid molecule encoding a multivalent protective compound. Particularly preferred nucleic acid molecules include $nDiVA_{833}$, $nDiVA_{672}$, $nDiVA_{663}$, $nDiVA_{615}$, $nDiVA_{726}$, $nDiVA_{678}$, $nOvVA_{330}$ and $nOvVA_{216}$.

The present invention also includes nucleic acid molecules encoding a protein having at least a portion of SEQ ID NO:2, nucleic acid molecules encoding a protein having at least a portion of SEQ ID NO:5, and nucleic acid molecules encoding a protein having at least a portion of SEQ ID NO:7, including nucleic acid molecules that have been modified to accommodate codon usage properties of the cells in which such nucleic acid molecules are to be expressed.

Knowing the nucleic acid sequences of certain parasitic helminth VA5 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain VA5 nucleic acid molecules for other parasitic helminths, particularly since, as described in detail in the Examples section, knowledge of *D. immitis* VA5 nucleic acid molecules of the present invention enabled the isolation of *O. volvulus* VA5 nucleic acid molecules of the present invention. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3 larval libraries as well as genomic DNA libraries. Similarly, preferred DNA sources to screen or from which to amplify nucleic acid molecules include parasitic helminth L3 larval DNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising parasitic helminth VA5 genes or other parasitic helminth VA5 nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit VA5 protein production or activity. Such therapeutic applications include the use of such oligonucleotides in, for example, antisense-, triplex formation-, ribozyme- and/or RNA drug-based technologies. The present invention, therefore, includes such oligonucleotides and methods to protect animals from disease caused by parasitic helminths by use of one or more of such technologies. Appropriate oligonucleotide-containing therapeutic compositions can be administered to an animal, using techniques known to those skilled in the art, either prior to or after infection by a parasitic helminth such as *D. immitis* or *O. volvulus* in order to protect the animal from disease.

The present invention also includes a recombinant vector, which includes at least one parasitic helminth VA5 nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth VA5 nucleic acid molecules of the present invention. One type of recombinant vector, referred to herein as a recombinant molecule and described in more detail below, can be used in the expression of nucleic acid molecules of the present invention. Preferred recombinant vectors are capable of replicating in the transformed cell.

Suitable and preferred nucleic acid molecules to include in recombinant vectors of the present invention are as disclosed herein for suitable and preferred parasitic helminth VA5 nucleic acid molecules per se. Particularly preferred nucleic acid molecules to include in recombinant vectors, and particularly in recombinant molecules, of the present invention include $nDiVA_{833}$, $nDiVA_{672}$, $nDiVA_{663}$, $nDiVA_{615}$, $nDiVA_{726}$, $nDiVA_{678}$, $nOvVA_{330}$ and $nOvVA_{216}$.

Isolated parasitic helminth VA5 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred parasitic helminth VA5 nucleic acid molecules per se. Particularly preferred nucleic acid molecules to include in recombinant cells of the present invention include $nDiVA_{833}$, $nDiVA_{672}$, $nDiVA_{663}$, $nDiVA_{615}$, $nDiVA_{726}$, $nDiVA_{678}$, $nOvVA_{330}$ and $nOvVA_{216}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing parasitic helminth VA5 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1$_x$3987 and SR-11 $_x$4072; *Spodoptera frugiperda*; *Trichoplusia ni*; BHK cells; MDCK cells; CRFK cells; CV-1 cells; COS cells; Vero cells and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells and/or HeLa cells.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types heretofore disclosed.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Suitable signal segments include natural signal segments (e.g., a parasitic helminth VA5 signal segment) or any heterologous signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (λ) (such as $\lambda p_L$ and $\lambda p_R$ and fusions that include such promoters), bacteriophage T7, T71ac, bacteriophage T3, bacteriophage SP6, bacteriophage SP01, metallothionein, α-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, poxvirus, adenovirus, cytomegalovirus (such as intermediate early promoters, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a parasitic helminth, such as a *D. immitis* or *O. volvulus* molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pβgal-nDiVA$_{833}$, pHis-nDiVA$_{678}$, pVLI393-nDiVA$_{726}$, pβgal-nOvVA$_{330}$, pHis-novvA$_{216}$, and pVLI393-nOvVA$_{216}$. Details regarding the production of *D. immitis* VA5 nucleic acid molecule-containing recombinant molecules is disclosed herein. *O. volvulus* VA5 recombinant molecules are produced in cesimilar manner.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli*:pβgal-nDiVA$_{833}$, *E. coli*:pHis-nDiVA$_{678}$, *S. frugiperda*:pVL1393-nDiVA$_{726}$, *E. coli*:pβgal-nOvVA$_{330}$, E. coli:pHis-nOvVA$_{216}$, and S. frugiperda:pVL1393-nOvVA$_{216}$. Details regarding the production of these recombinant cells is disclosed herein.

Recombinant cells of the present invention can also be co-transformed with one or more recombinant molecules including parasitic helminth VA5 nucleic acid molecules encoding one or more proteins of the present invention and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a parasitic helminth VA5 protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in E. coli; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a parasitic helminth VA5 protein of the present invention or to a mimetope thereof. Such antibodies are also referred to herein as anti-parasitic helminth VA5 antibodies. Particularly preferred antibodies of this embodiment include anti-D. immitis VA5 antibodies and anti-O. volvulus VA5 antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid. An anti-parasitic helminth VA5 antibody preferably binds to a parasitic helminth VA5 protein in such a way as to reduce the activity of that protein.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce parasitic helminth VA5 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: (a) an isolated parasitic helminth venom allergen antigen 5-like protein or a mimetope thereof; (b) an isolated parasitic helminth nucleic acid molecule that hybridizes under stringent hybridization conditions with a *D. immitis* venom allergen antigen 5-like gene and/or an *O. volvulus* venom allergen antigen 5-like gene; (c) an isolated antibody that selectively binds to a parasitic helminth venom allergen antigen 5-like protein; and (d) a mixture (i.e., combination) of at least two of the compounds. As used herein, a protective compound refers to a compound that, when administered to an animal in an effective manner, is able to treat, ameliorate, and/or prevent disease caused by a parasitic helminth of the present invention. Preferred helminths to target are heretofore disclosed. Examples of proteins, nucleic acid molecules and antibodies of the present invention are disclosed herein.

The present invention also includes a therapeutic composition comprising at least one parasitic helminth VA5-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred. Preferred animals to protect against onchocerciasis include humans, cattle and horses, with humans being particularly preferred.

In one embodiment, a therapeutic composition of the present invention can be administered to the vector in which the parasitic helminth develops, such as to a mosquito in order to prevent the spread of heartworm or to a black fly in order to prevent the spread of onchocerciasis. Such administration could be orally or by developing transgenic vectors capable of producing at least one therapeutic composition of the present invention. In another embodiment, a vector, such as a mosquito of a black fly, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o- cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment for preferably at least about 1 month, more preferably at least about 3 months and even more preferably for at least about 6 months, even more preferably for at leven moret 9 months, and even more preferably for at least about 12 months.

In order to protect an animal from disease caused by a parasitic helminth of the present invention, a therapeutic composition of the present invention is administered to the animal in an effective manner such that the composition is capable of protecting that animal from a disease caused by a parasitic helminth. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of parasitic helminth VA5 proteins in order to interfere with development of parasitic helminths targeted in accordance with the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 µg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

A recombinant virus vaccine of the present invention includes a recombinant molecule of the present invention that is packaged in a viral coat and that can be expressed in an animal after administration. Preferably, the recombinant molecule is packaging-deficient. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), species-specific herpesviruses and species-specific poxviruses. Methods to produce and use recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminths as disclosed herein. For example, a recombinant virus vaccine comprising a D. immitis VA5 nucleic acid molecule of the present invention is administered according to a protocol that results in the animal producing a sufficient immune response to protect itself from heartworm. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells include Salmonella, E. coli, Listeria, Mycobacterium, *S. frugiperda*, BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

One preferred embodiment of the present invention is the use of parasitic helminth VA5 proteins, nucleic acid molecules and antibodies of the present invention, and particularly *D. immitis* VA5 proteins, nucleic acid molecules and antibodies of the present invention, to protect an animal from heartworm. Preferred therapeutic compositions are those that are able to inhibit at least one step in the portion of the parasite's development cycle that includes L3 larvae, third molt, L4 larvae, fourth molt and immature adult prior to entering the circulatory system. In dogs, this portion of the development cycle is about 70 days. Particularly preferred therapeutic compositions include *D. immitis*-based therapeutic compositions of the present invention. Such compositions are administered to animals in a manner effective to protect the animals from heartworm. Additional protection may be obtained by administering additional protective compounds, including other *D. immitis* proteins, nucleic acid molecules and antibodies.

Another preferred embodiment of the present invention is the use of parasitic helminth VA5 proteins, nucleic acid molecules and antibodies of the present invention, and particularly *O. volvulus* VA5 proteins, nucleic acid molecules and antibodies of the present invention, to protect a human from onchocerciasis. Preferred therapeutic compositions are those that are able to inhibit at least one step in the portion of the parasite's development cycle that includes L3 larvae, third molt, L4 larvae, fourth molt and immature adult prior to entering the subcutaneous tissues. In humans infected with *O. volvulus*, this portion of the development cycle is about 150 days. Particularly preferred therapeutic compositions include *O. volvulus*-based therapeutic compositions of the present invention. Such compositions are administered to humans in a manner effective to protect the treated humans from onchocerciasis. Additional protection may be obtained by administering additional protective compounds, including other Onchocerca, preferably *O. volvulus*, proteins, nucleic acid molecules and antibodies.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle.

The following examples are provided for the purposes of illustration and are not intended to limit the scope of the present invention.

EXAMPLES

Example 1

This Example describes the cloning and sequencing of a parasitic helminth VA5 nucleic acid molecule of the present invention.

A *D. immitis* VA5 nucleic acid molecule of about 833 nucleotides, denoted $nDiVA_{833}$, was identified by its ability to encode a protein that selectively bound to at least one component of immune serum collected from a dog immunized with *D. immitis* larvae in the following manner. A *D. immitis* cDNA expression library was constructed in Uni-ZAP™ XR vector (available from Stratagene Cloning Systems, La Jolla, Calif.), using Stratagene's ZAP-cDNA Synthesis Kit protocol and third stage larval mRNAs. Using the protocol described in the Stratagene picoBlue immunoscreening kit, the L3 larval cDNA expression library was screened with immune dog sera. The production and use of immune dog serum to identify heartworm vaccine candidates is disclosed in U.S. patent application Ser. No. 08/101,283, filed Aug. 3, 1993, which is incorporated by reference herein in its entirety. Ser. No. 08/101,283 is a continuation of U.S. patent application Ser. No. 07/654,226, filed Feb. 12, 1991, also published as PCT Publication No. WO 92/13560 on Aug. 20, 1992.

Immunoscreening of duplicate plaque lifts of the cDNA library with the same immune dog serum identified several plaques which were converted into double-stranded plasmids using ExAssist™ helper phage and SOLR™ *E. coli* according to the in vivo excision protocol described in the Stratagene ZAP-CDNA Synthesis Kit. Double-stranded plasmid DNA was prepared from four independent clones, using an alkaline lysis protocol, such as that described in Sambrook et al., ibid. Each plasmid DNA was digested with EcoRI and XhoI restriction endonucleases. Digestion of one of the plasmids released a *D. immitis* DNA fragment of about 833 nucleotides, which by DNA sequence analysis (described in detail below) was shown to encode a venom allergen antigen 5-like protein. The *D. immitis* DNA fragment is denoted herein as nucleic acid molecule $nDiVA_{833}$. The double-stranded plasmid containing the fragment is denoted herein as recombinant molecule $p\beta gal\text{-}nDiVA_{833}$. Surprisingly, the protein expressed by recombinant molecule $p\beta gal\text{-}nDiVA_{833}$ was not recognized by immune dog serum in immunoblot experiments. Since the other three double-stranded plasmids encoded proteins that were recognized by immune dog serum in immunoblot experiments and that were not venom allergen-like proteins, it is believed that nucleic acid molecule $nDiVA_{833}$ was fortuitously co-isolated with plaques that expressed proteins selectively recognized by immune dog serum.

Nucleic acid molecule $nDiVA_{833}$ was sequenced using the Sanger dideoxy chain termination method, as described in Sambrook et al., ibid. An about 833 nucleotide consensus sequence of the entire nucleic acid molecule was determined and is presented as SEQ ID NO:1. The nucleic acid sequence SEQ ID NO:1 includes an open reading frame spanning from about nucleotide 45 through about nucleotide 719, with a first ATG codon spanning from about nucleotide 54 through about nucleotide 56 and a termination (stop) codon spanning from about nucleotide 717 through bout 719. Assuming that this ATG represents the initiation (start) codon, SEQ ID NO:1 encodes a protein having an amino acid sequence of about 221 amino acids, denoted herein as $PDiVA_{221}$, the amino acid sequence of which is presented in SEQ ID NO:2. $PDiVA_{221}$ is encoded by a nucleic acid sequence of about 663 nucleotides, denoted herein as nucleic acid molecule nDiVA$_{663}$, the nucleic acid sequence of which is represented herein as SEQ ID NO:3. It is to be noted, however, that the open frame of nDiVA$_{833}$ extends an additional 9 nucleotides upstream from the first ATG codon, upstream of which is the stop codon TAA. That open reading frame, denoted herein as nDiVA$_{672}$, would encode a protein of 224 amino acids, denoted herein as PDiVA$_{224}$, the first three amino acids being phenylalanine, cysteine, and lysine. SEQ ID NO:1 also includes a putative polyadenylation signal (5' AATAAA 3') spanning from about nucleotide 799 through about nucleotide 805.

Analysis of SEQ ID NO:2 suggests the presence of a signal peptide encoded by a stretch of amino acids spanning from about amino acid 1 through about amino acid 16. The proposed mature, processed protein, denoted herein as PDiVA$_{205}$, is encoded by a nucleic acid molecule of about 615 nucleotides, denoted herein as nDiVA$_{615}$ having nucleic acid sequence SEQ ID NO:4, the deduced amino acid sequence of which is represented by SEQ ID NO:5. PDiVA$_{205}$ has a calculated molecular weight of about 23.5 kD and an estimated pI of about 9.75.

A homology search of the non-redundant protein sequence database was performed through the National Center for Biotechnology Information using the BLAST network. This database includes +SwissProt+PIR+SPUpdate+GenPept+GPUpdate. The search was performed using SEQ ID NO:2 and showed that SEQ ID NO:2 showed significant homology to certain venom allergens. That is, comparison of amino acid sequence SEQ ID NO:2 with amino acid sequences reported in GenBank indicates that SEQ ID NO:2 shares the following percent identities with the amino acid sequences of the following hymenopteran insect proteins: about 25% identical to fire ant venom allergen III (Acc. No. P35788); about 24% identical to white fact hornet venom allergen 5-3 (Acc. No. P10737); and about 24% identical to European hornet venom allergen 5-2 (Acc. No. P35782). SEQ ID NO:2 also shares about 27% identity with Mexican beaded lizard helothermine (Acc. No. U13619), about 27% identity with human testis-specific protein TPX-1 precursor (Acc. No. P16562), about 26% identity with mouse testis-specific protein TPX-1 precursor (Acc No. P16563), about 13% identity with hookworm *Ancylostoma caninum* neutrophil inhibitory factor precursor (Acc. No. A54419), and about 24% identity with mouse sperm-coating glycoprotein 1 precursor (Acc. No. Q03401).

Comparison of SEQ ID NO:3 with nucleic acid sequences reported in GenBank indicates that SEQ ID NO:3 is about 51% identical to the *Vespula vulgaris* (yellow jacket) venom allergen 5 gene, and about 46% identical to the *Dolichovespula maculata* (white-face hornet) venom allergen 5 gene.

Example 2

This example discloses the production of a recombinant cell of the present invention.

Recombinant molecule pHis-nDiVA$_{678}$, containing *D. immitis* nucleic acid molecule nDiVA$_{678}$ operatively linked to trc transcription control sequences and to a fusion sequence encoding a poly-histidine segment comprising 6 histidines, was produced in the following manner. An about 678 nucleotide DNA fragment containing nucleotides spanning from about nucleotide 102 through about nucleotide 779 of SEQ ID NO:1, called $nDiVA_{678}$, was PCR amplified from recombinant molecule pβgal-$nDiVA_{833}$, produced as described in Example 1, using the following primers: sense primer VA sen, which has nucleic acid sequence 5' CGTTGTTGTGGATCCTTATGAATGTGAAGGAGG 3' (BamHI site indicated in bold) that is represented herein as SEQ ID NO:9; and antisense primer VA ant, which has nucleic acid sequence 5' ATTAATCTGCAGTTACCCTTGTAAAATATCAAATATATG 3' (PstI site indicated in bold) that is represented herein as SEQ ID NO:10. The PCR product was digested with BamHI and PstI restriction endonucleases, gel purified and directionally subcloned into expression vector pTrcHisB (available from Invitrogen, San Diego, Calif.) that had been cleaved with BamHI and PstI. The resulting recombinant molecule, denoted herein as pHis-$nDiVA_{678}$, was transformed into *E. coli* to form recombinant cell *E. coli*:pHis-$nDiVA_{678}$.

Example 3

This Example describes the production in bacteria of a parasitic helminth protein of the present invention. This Example also discloses an antibody preparation produced in response to the parasitic helminth protein.

Recombinant cell *E. coli*:pHis-$nDiVA_{678}$1 produced as described in Example 2, was cultured in shake flasks containing an enriched bacterial growth medium containing 0.1 mg/ml ampicillin and 0.1% glucose at about 32° C. When the cells reached an $OD_{600}$ of about 0.4, expression of *D. immitis* nucleic acid molecule $nDiVA_{678}$ was induced by addition of about 0.5 mM isopropyl-β-D-thiogalactoside (IPTG), and the cells cultured for about 3 hours at about 32° C. Protein production was monitored by SDS PAGE of recombinant cell lysates, followed by Coomassie blue staining, using standard techniques. Recombinant cell *E. coli*:pHis-$nDiVA_{678}$ produced a fusion protein, denoted herein as PHIS-$PDiVA_{205}$, that migrated with an apparent molecular weight of about 30 kD.

Immunoblot analysis of recombinant cell *E. coli*:pHis-$nDiVA_{678}$ lysates indicated that the about 30 kD protein is able to bind to a T7 tag monoclonal antibody (available from Novagen, Inc., Madison, Wis.) directed against the fusion portion of the recombinant PHIS-$PDiVA_{205}$ fusion protein.

The PHIS-$PDiVA_{205}$ histidine fusion peptide was separated from soluble *E. coli* proteins by nickel chelation chromatography and an imidazole gradient. Immunoblot analysis of the total *E. coli*:pHis-$nDiVA_{678}$ lysate, column eluate and column void volume using the T7 tag monoclonal antibody indicated that the PHIS-$PDiVA_{205}$ 30 kD protein bound to the nickel column and was eluted using an imidazole gradient.

A rabbit was immunized twice with PHIS-$PDiVA_{205}$ that had been purified by chelation chromatography. Antisera collected from this rabbit was denoted anti-PHIS-$PDiVA_{205}$ antisera.

Example 4

This Example describes the production of a eukaryotic recombinant cell and use of that cell to produce a parasitic helminth protein of the present invention.

Recombinant molecule pVL1393-$nDiVA_{726}$, containing *D. immitis* nucleic acid molecule $nDiVA_{726}$ operatively linked to baculovirus polyhedron transcription control sequences, was produced in the following manner. An about 726 nucleotide DNA fragment containing nucleotides spanning from about nucleotide 54 through about nucleotide 779 of SEQ ID NO:1, called $nDiVA_{726}$, was PCR amplified from recombinant molecule pβgal-$nDiVA_{833}$, produced as described in Example 1, using the following primers: sense primer BVVA sen, which has nucleic acid sequence 5' CGCGGATCCTATAAATATGATACTTTTGGTTAT 3' (BamHI indicated in bold) that is represented herein as SEQ ID NO:11; and antisense primer BvVA ant, which has nucleic acid sequence 5' GGCCTTAAGTTACCCTTG-TAAAATAT 3' (EcoRI site indicated in bold) that is represented herein as SEQ ID NO:12. The sense primer was designed from nDiVA$_{833}$ sequence with modifications to enhance expression in the baculovirus system. The PCR product was digested with BamHI and EcoRI restriction endonucleases, gel purified and directionally subcloned into baculovirus shuttle plasmid pVL1393 (available from Invitrogen) that had been cleaved with BamHI and EcoRI. The resulting recombinant molecule, denoted herein as pVL1393-nDiVA$_{726}$, was co-transfected into S. frugiperda Sf9 cells (donated by the Colorado Bioprocessing Center, Fort Collins, Colo.) with linear wild type baculovirus DNA (ACMNPV) and insectin cationic liposomes (available from Invitrogen) to form S. frugiperda:pVL1393-nDiVA$_{726}$.

The resulting recombinant virus, denoted Bv-nDiVA$_{726}$, was cultivated for increased production of recombinant virus and to verify expression of PDiVA$_{221}$ as a protein of about 26 kD, as determined by SDS PAGE.

Example 5

This Example demonstrates the use of a D. immitis nucleic acid molecule of the present invention to obtain a nucleic acid molecule of another parasitic helminth.

O. volvulus nucleic acid molecule nOvVA$_{330}$ was obtained in the following manner. D. immitis nucleic acid molecule nDiVA$_{833}$ was mixed hexamer labeled with the Megaprime DNA Labeling System (available from Amersham Corp., Arlington Heights, Ill.) and used to screen an O. volvulus L3 cDNA library for plaques having nucleic acid molecules that could form stable hybrids with nDiVA$_{833}$ under stringent hybridization conditions. About 70,000 plaques from the library were screened with the labeled D. immitis nucleic acid molecule using standard hybridization techniques as described by Sambrook et al., ibid. After several rounds of hybridization and selection of plaques hybridizing to nDiVA$_{833}$, four L3 cDNA clones were plaque purified, excised and subcloned into pBluescript (available from Stratagene). Resultant plasmids corresponding to each of the four clones were restricted with EcoRI restriction endonuclease and found to contain inserts of about 350 nucleotides.

Each of the inserts was sequenced as described in Example 1 and determined to have the same about 330-nucleotide nucleic acid sequence, represented herein as SEQ ID NO:6. A nucleic acid molecule consisting of SEQ ID NO:6 is referred to herein as nOvVA$_{330}$. Translation of SEQ ID NO:6 indicates that nOvVA$_{330}$ includes an open reading frame spanning from about nucleotide 1 through about nucleotide 219 with a stop codon nucleotides spanning from about nucleotide 217 through about nucleotide 219, followed by a 3' untranslated region spanning from about nucleotide 220 through about nucleotide 330. The open reading frame encodes a protein of about 72 amino acids, referred to herein as POvVA$_{72}$, the amino acid sequence of which is represented herein as SEQ ID NO:7. Nucleic acid sequence nOvVA$_{216}$, represented herein as SEQ ID NO:8, consists of the nucleotides encoding POvVA$_{72}$.

Comparison of the coding region of O. volvulus nOvVA$_{330}$ with the corresponding carboxyl terminal coding region of D. immitis nDiVA$_{833}$ indicates that the two nucleotide sequences share about 77% identity. The corresponding amino acid sequences are about 64% identical. About 72% identity is found between nOvVA$_{330}$ (i.e., the coding region and 3' untranslated region) and the corresponding region of nDiVA$_{833}$.

A homology search of the non-redundant protein sequence database was performed as described in Example 1. Comparison of amino acid sequence SEQ ID NO:7 with reported amino acid sequences indicates that SEQ ID NO:7 is about 42% identical over a region of about 48 amino acids to the amino acid sequence of the Dolichovespula maculata (white-face hornet) venom allergen 5 protein, about 40% identical over a region of about 48 amino acids to the amino acid sequences of the Vespa crabro (European hornet) and Dolichovespula arenaria (yellow hornet) venom allergen 5 proteins, about 37% identical over a region of about 49 amino acids to the amino acid sequence of the Solenopsis invicta (red imported fire ant) venom allergen 5 protein, and about 33% identical over a region of about 48 amino acids to the amino acid sequence of the Vespula vulgaris (yellow jacket) venom allergen 5 protein.

Comparison of SEQ ID NO:8 with nucleic acid sequences reported in GenBank indicates that SEQ ID NO:8 is about 56% identical with the Vespula vulgaris (yellow jacket) venom allergen 5 gene, and about 61% identical over a region of about 181 nucleotides with the Dolichovespula maculata (white-face hornet) venom allergen 5 gene.

This example clearly indicates that knowledge of the nucleic acid sequence of a parasitic helminth VA5 nucleic acid molecule of the present invention enables the identification and isolation of parasitic helminth nucleic acid molecules of a species distinct from that having the known sequence.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 833 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 54..716

( x i ) SEQUENCE DESCRIPTION: SEQ ID NO:1:

```
ATATTTGCTA AAGTGATATC TTCTATTGTA ACTTTATCAG ATAATTTGC AAA ATG      56
                                                            Met
                                                            1

ATA CTT TTG GTT ATT TTC CCT GCA ATT ATC GTT GTT GTG GCA AGT TAT   104
Ile Leu Leu Val Ile Phe Pro Ala Ile Ile Val Val Val Ala Ser Tyr
             5                  10                  15

GAA TGT GAA GGA GGT AAA TTA ACA CCA ACG GAA CGT AAA AAT ATT GTT   152
Glu Cys Glu Gly Gly Lys Leu Thr Pro Thr Glu Arg Lys Asn Ile Val
         20                  25                  30

ACA CAG ATT AAT AAA TAT CGC TCT CGA TTA ATT CGT GGA AAA CTT AAA   200
Thr Gln Ile Asn Lys Tyr Arg Ser Arg Leu Ile Arg Gly Lys Leu Lys
     35                  40                  45

AAT AAA GAT GGT TAT TTG ATG CCA AAA GGC AAG AAT ATG TTG AGA ATG   248
Asn Lys Asp Gly Tyr Leu Met Pro Lys Gly Lys Asn Met Leu Arg Met
 50                  55                  60                  65

AGA TGG GAT TGT AAG TTA GAA AAA TCG GCA CAA AAC TGG GCA AAT ATG   296
Arg Trp Asp Cys Lys Leu Glu Lys Ser Ala Gln Asn Trp Ala Asn Met
                 70                  75                  80

TGT GTC TTT GGC CAT TCA CCA AGC AGC GAA AGA AGA GGA ATC GGT GAA   344
Cys Val Phe Gly His Ser Pro Ser Ser Glu Arg Arg Gly Ile Gly Glu
             85                  90                  95

AAT GTT TAC GCT TAC TGG TCA TCA GGA TCA GTT CGA GAT CTT AAA AAA   392
Asn Val Tyr Ala Tyr Trp Ser Ser Gly Ser Val Arg Asp Leu Lys Lys
        100                 105                 110

ACT GCT GGT ACG GAT GCT GGT AGA CTC TGG TGG TCA GAA CTT GAG AAA   440
Thr Ala Gly Thr Asp Ala Gly Arg Leu Trp Trp Ser Glu Leu Glu Lys
    115                 120                 125

TAC TAC AGC GAT AAT CCT TCG AAT AAT TTG ACT TCG GAA GTT GCC ATG   488
Tyr Tyr Ser Asp Asn Pro Ser Asn Asn Leu Thr Ser Glu Val Ala Met
130                 135                 140                 145

GAA AAT ATT CTT CAT TTT ACG CAG ATG GCT TGG GGT GAA ACG TAT AAA   536
Glu Asn Ile Leu His Phe Thr Gln Met Ala Trp Gly Glu Thr Tyr Lys
                150                 155                 160

CTT GGT TCG GGT GTT GAC CAC AAT ATT GTG ATG GTG GCA AGA ACA CTT   584
Leu Gly Ser Gly Val Asp His Asn Ile Val Met Val Ala Arg Thr Leu
            165                 170                 175

GTA TTT ATT TGT CAC TAT TTC CCC GGA GGA AAT ATG GTG AAA GAT TTG   632
Val Phe Ile Cys His Tyr Phe Pro Gly Gly Asn Met Val Lys Asp Leu
        180                 185                 190

ATA TAT GAG CTT GGT AAT CCA TGC AAA CAT AAC AAA GAT TGC CGT ACG   680
Ile Tyr Glu Leu Gly Asn Pro Cys Lys His Asn Lys Asp Cys Arg Thr
    195                 200                 205

AAA AGA TGC TCA GCA AAA TCT GGA TTG TGC AAA AAA TGAAAAAATT        726
Lys Arg Cys Ser Ala Lys Ser Gly Leu Cys Lys Lys
210                 215                 220

TTCATTTTCA ATATTTAATT TTTGTTCATA TATTTGATAT TTACAAGGG TAATATTTTA  786

TTAATTATTA TAAAATAAAC AACTGCAAAA AAAAAAAAAA AAAAAA               833
```

( 2 ) INFORMATION FOR SEQ ID NO:2:

( i ) SEQUENCE CHARACTERISTICS:
        ( A ) LENGTH: 221 amino acids
        ( B ) TYPE: amino acid
        ( D ) TOPOLOGY: linear (ii) MOLECULE TYPE: protein (xi) SEQUENCE DESCRIPTION: SEQ ID NO:2:

| Met | Ile | Leu | Leu | Val | Ile | Phe | Pro | Ala | Ile | Ile | Val | Val | Val | Ala | Ser |
|---|---|---|---|---|---|---|---|---|---|---|---|---|---|---|---|
| 1 | | | | 5 | | | | | 10 | | | | | 15 | |

| Tyr | Glu | Cys | Glu | Gly | Gly | Lys | Leu | Thr | Pro | Thr | Glu | Arg | Lys | Asn | Ile |
|---|---|---|---|---|---|---|---|---|---|---|---|---|---|---|---|
| | | | 20 | | | | | 25 | | | | | 30 | | |

| Val | Thr | Gln | Ile | Asn | Lys | Tyr | Arg | Ser | Arg | Leu | Ile | Arg | Gly | Lys | Leu |
|---|---|---|---|---|---|---|---|---|---|---|---|---|---|---|---|
| | | 35 | | | | | 40 | | | | | 45 | | | |

| Lys | Asn | Lys | Asp | Gly | Tyr | Leu | Met | Pro | Lys | Gly | Lys | Asn | Met | Leu | Arg |
|---|---|---|---|---|---|---|---|---|---|---|---|---|---|---|---|
| | 50 | | | | | 55 | | | | | 60 | | | | |

| Met | Arg | Trp | Asp | Cys | Lys | Leu | Glu | Lys | Ser | Ala | Gln | Asn | Trp | Ala | Asn |
|---|---|---|---|---|---|---|---|---|---|---|---|---|---|---|---|
| 65 | | | | | 70 | | | | | 75 | | | | | 80 |

| Met | Cys | Val | Phe | Gly | His | Ser | Pro | Ser | Ser | Glu | Arg | Arg | Gly | Ile | Gly |
|---|---|---|---|---|---|---|---|---|---|---|---|---|---|---|---|
| | | | | 85 | | | | | 90 | | | | | 95 | |

| Glu | Asn | Val | Tyr | Ala | Tyr | Trp | Ser | Ser | Gly | Ser | Val | Arg | Asp | Leu | Lys |
|---|---|---|---|---|---|---|---|---|---|---|---|---|---|---|---|
| | | | 100 | | | | | 105 | | | | | 110 | | |

| Lys | Thr | Ala | Gly | Thr | Asp | Ala | Gly | Arg | Leu | Trp | Trp | Ser | Glu | Leu | Glu |
|---|---|---|---|---|---|---|---|---|---|---|---|---|---|---|---|
| | | 115 | | | | | 120 | | | | | 125 | | | |

| Lys | Tyr | Tyr | Ser | Asp | Asn | Pro | Ser | Asn | Asn | Leu | Thr | Ser | Glu | Val | Ala |
|---|---|---|---|---|---|---|---|---|---|---|---|---|---|---|---|
| | 130 | | | | | 135 | | | | | 140 | | | | |

| Met | Glu | Asn | Ile | Leu | His | Phe | Thr | Gln | Met | Ala | Trp | Gly | Glu | Thr | Tyr |
|---|---|---|---|---|---|---|---|---|---|---|---|---|---|---|---|
| 145 | | | | | 150 | | | | | 155 | | | | | 160 |

| Lys | Leu | Gly | Ser | Gly | Val | Asp | His | Asn | Ile | Val | Met | Val | Ala | Arg | Thr |
|---|---|---|---|---|---|---|---|---|---|---|---|---|---|---|---|
| | | | | 165 | | | | | 170 | | | | | 175 | |

| Leu | Val | Phe | Ile | Cys | His | Tyr | Phe | Pro | Gly | Gly | Asn | Met | Val | Lys | Asp |
|---|---|---|---|---|---|---|---|---|---|---|---|---|---|---|---|
| | | | 180 | | | | | 185 | | | | | 190 | | |

| Leu | Ile | Tyr | Glu | Leu | Gly | Asn | Pro | Cys | Lys | His | Asn | Lys | Asp | Cys | Arg |
|---|---|---|---|---|---|---|---|---|---|---|---|---|---|---|---|
| | | 195 | | | | | 200 | | | | | 205 | | | |

| Thr | Lys | Arg | Cys | Ser | Ala | Lys | Ser | Gly | Leu | Cys | Lys | Lys |
|---|---|---|---|---|---|---|---|---|---|---|---|---|
| 210 | | | | | 215 | | | | | 220 | | |

(2) INFORMATION FOR SEQ ID NO:3:

(i) SEQUENCE CHARACTERISTICS:
(A) LENGTH: 663 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

| ATGATACTTT | TGGTTATTTT | CCCTGCAATT | ATCGTTGTTG | TGGCAAGTTA | TGAATGTGAA | 60 |
| GGAGGTAAAT | TAACACCAAC | GGAACGTAAA | AATATTGTTA | CACAGATTAA | TAAATATCGC | 120 |
| TCTCGATTAA | TTCGTGGAAA | ACTTAAAAAT | AAAGATGGTT | ATTTGATGCC | AAAAGGCAAG | 180 |
| AATATGTTGA | GAATGAGATG | GGATTGTAAG | TTAGAAAAAT | CGGCACAAAA | CTGGGCAAAT | 240 |
| ATGTGTGTCT | TTGGCCATTC | ACCAAGCAGC | GAAAGAAGAG | GAATCGGTGA | AAATGTTTAC | 300 |
| GCTTACTGGT | CATCAGGATC | AGTTCGAGAT | CTTAAAAAAA | CTGCTGGTAC | GGATGCTGGT | 360 |
| AGACTCTGGT | GGTCAGAACT | TGAGAAATAC | TACAGCGATA | ATCCTTCGAA | TAATTTGACT | 420 |
| TCGGAAGTTG | CCATGGAAAA | TATTCTTCAT | TTTACGCAGA | TGGCTTGGGG | TGAAACGTAT | 480 |
| AAACTTGGTT | CGGGTGTTGA | CCACAATATT | GTGATGGTGG | CAAGAACACT | TGTATTTATT | 540 |
| TGTCACTATT | TCCCCGGAGG | AAATATGGTG | AAAGATTTGA | TATATGAGCT | TGGTAATCCA | 600 |
| TGCAAACATA | ACAAAGATTG | CCGTACGAAA | AGATGCTCAG | CAAAATCTGG | ATTGTGCAAA | 660 |

AAA 663

(2) INFORMATION FOR SEQ ID NO:4:

(i) SEQUENCE CHARACTERISTICS:
        (A) LENGTH: 615 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..615

(xi) SEQUENCE DESCRIPTION: SEQ ID NO:4:

```
TAT GAA TGT GAA GGA GGT AAA TTA ACA CCA ACG GAA CGT AAA AAT ATT        48
Tyr Glu Cys Glu Gly Gly Lys Leu Thr Pro Thr Glu Arg Lys Asn Ile
 1               5                  10                  15

GTT ACA CAG ATT AAT AAA TAT CGC TCT CGA TTA ATT CGT GGA AAA CTT        96
Val Thr Gln Ile Asn Lys Tyr Arg Ser Arg Leu Ile Arg Gly Lys Leu
             20                  25                  30

AAA AAT AAA GAT GGT TAT TTG ATG CCA AAA GGC AAG AAT ATG TTG AGA       144
Lys Asn Lys Asp Gly Tyr Leu Met Pro Lys Gly Lys Asn Met Leu Arg
         35                  40                  45

ATG AGA TGG GAT TGT AAG TTA GAA AAA TCG GCA CAA AAC TGG GCA AAT       192
Met Arg Trp Asp Cys Lys Leu Glu Lys Ser Ala Gln Asn Trp Ala Asn
     50                  55                  60

ATG TGT GTC TTT GGC CAT TCA CCA AGC AGC GAA AGA AGA GGA ATC GGT       240
Met Cys Val Phe Gly His Ser Pro Ser Ser Glu Arg Arg Gly Ile Gly
 65                  70                  75                  80

GAA AAT GTT TAC GCT TAC TGG TCA TCA GGA TCA GTT CGA GAT CTT AAA       288
Glu Asn Val Tyr Ala Tyr Trp Ser Ser Gly Ser Val Arg Asp Leu Lys
                 85                  90                  95

AAA ACT GCT GGT ACG GAT GCT GGT AGA CTC TGG TGG TCA GAA CTT GAG       336
Lys Thr Ala Gly Thr Asp Ala Gly Arg Leu Trp Trp Ser Glu Leu Glu
            100                 105                 110

AAA TAC TAC AGC GAT AAT CCT TCG AAT AAT TTG ACT TCG GAA GTT GCC       384
Lys Tyr Tyr Ser Asp Asn Pro Ser Asn Asn Leu Thr Ser Glu Val Ala
        115                 120                 125

ATG GAA AAT ATT CTT CAT TTT ACG CAG ATG GCT TGG GGT GAA ACG TAT       432
Met Glu Asn Ile Leu His Phe Thr Gln Met Ala Trp Gly Glu Thr Tyr
    130                 135                 140

AAA CTT GGT TCG GGT GTT GAC CAC AAT ATT GTG ATG GTG GCA AGA ACA       480
Lys Leu Gly Ser Gly Val Asp His Asn Ile Val Met Val Ala Arg Thr
145                 150                 155                 160

CTT GTA TTT ATT TGT CAC TAT TTC CCC GGA GGA AAT ATG GTG AAA GAT       528
Leu Val Phe Ile Cys His Tyr Phe Pro Gly Gly Asn Met Val Lys Asp
                165                 170                 175

TTG ATA TAT GAG CTT GGT AAT CCA TGC AAA CAT AAC AAA GAT TGC CGT       576
Leu Ile Tyr Glu Leu Gly Asn Pro Cys Lys His Asn Lys Asp Cys Arg
            180                 185                 190

ACG AAA AGA TGC TCA GCA AAA TCT GGA TTG TGC AAA AAA                   615
Thr Lys Arg Cys Ser Ala Lys Ser Gly Leu Cys Lys Lys
        195                 200                 205
```

(2) INFORMATION FOR SEQ ID NO:5:

(i) SEQUENCE CHARACTERISTICS:
        (A) LENGTH: 205 amino acids
        (B) TYPE: amino acid
        (D) TOPOLOGY: linear ( i i ) MOLECULE TYPE: protein ( x i ) SEQUENCE DESCRIPTION: SEQ ID NO:5:

| Tyr | Glu | Cys | Glu | Gly | Gly | Lys | Leu | Thr | Pro | Thr | Glu | Arg | Lys | Asn | Ile |
|-----|-----|-----|-----|-----|-----|-----|-----|-----|-----|-----|-----|-----|-----|-----|-----|
| 1 | | | | 5 | | | | | 10 | | | | | 15 | |

| Val | Thr | Gln | Ile | Asn | Lys | Tyr | Arg | Ser | Arg | Leu | Ile | Arg | Gly | Lys | Leu |
| | | | 20 | | | | | 25 | | | | | 30 | | |

| Lys | Asn | Lys | Asp | Gly | Tyr | Leu | Met | Pro | Lys | Gly | Lys | Asn | Met | Leu | Arg |
| | | 35 | | | | | 40 | | | | | 45 | | | |

| Met | Arg | Trp | Asp | Cys | Lys | Leu | Glu | Lys | Ser | Ala | Gln | Asn | Trp | Ala | Asn |
| | 50 | | | | | 55 | | | | | 60 | | | | |

| Met | Cys | Val | Phe | Gly | His | Ser | Pro | Ser | Ser | Glu | Arg | Arg | Gly | Ile | Gly |
| 65 | | | | | 70 | | | | | 75 | | | | | 80 |

| Glu | Asn | Val | Tyr | Ala | Tyr | Trp | Ser | Ser | Gly | Ser | Val | Arg | Asp | Leu | Lys |
| | | | | 85 | | | | | 90 | | | | | 95 | |

| Lys | Thr | Ala | Gly | Thr | Asp | Ala | Gly | Arg | Leu | Trp | Trp | Ser | Glu | Leu | Glu |
| | | | | 100 | | | | | 105 | | | | | 110 | |

| Lys | Tyr | Tyr | Ser | Asp | Asn | Pro | Ser | Asn | Leu | Thr | Ser | Glu | Val | Ala |
| | | 115 | | | | | 120 | | | | | 125 | | |

| Met | Glu | Asn | Ile | Leu | His | Phe | Thr | Gln | Met | Ala | Trp | Gly | Glu | Thr | Tyr |
| | 130 | | | | | 135 | | | | | 140 | | | | |

| Lys | Leu | Gly | Ser | Gly | Val | Asp | His | Asn | Ile | Val | Met | Val | Ala | Arg | Thr |
| 145 | | | | | 150 | | | | | 155 | | | | | 160 |

| Leu | Val | Phe | Ile | Cys | His | Tyr | Phe | Pro | Gly | Gly | Asn | Met | Val | Lys | Asp |
| | | | | 165 | | | | | 170 | | | | | 175 | |

| Leu | Ile | Tyr | Glu | Leu | Gly | Asn | Pro | Cys | Lys | His | Asn | Lys | Asp | Cys | Arg |
| | | | 180 | | | | | 185 | | | | | 190 | | |

| Thr | Lys | Arg | Cys | Ser | Ala | Lys | Ser | Gly | Leu | Cys | Lys | Lys |
| | | 195 | | | | | 200 | | | | | 205 |

( 2 ) INFORMATION FOR SEQ ID NO:6:

( i ) SEQUENCE CHARACTERISTICS:
( A ) LENGTH: 330 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..218

( x i ) SEQUENCE DESCRIPTION: SEQ ID NO:6:

| TTG | CAT | TTC | ACA | CAA | ATG | GCT | TGG | GGT | AAG | ACT | TAT | AAA | ATT | GGT | TGC | 48 |
| Leu | His | Phe | Thr | Gln | Met | Ala | Trp | Gly | Lys | Thr | Tyr | Lys | Ile | Gly | Cys | |
| 1 | | | | 5 | | | | | 10 | | | | | 15 | | |

| GGT | GTT | GCA | ACA | CAA | TGT | GAT | GGT | GGT | AGA | ACA | CTT | ATT | GTT | ATT | TGT | 96 |
| Gly | Val | Ala | Thr | Gln | Cys | Asp | Gly | Gly | Arg | Thr | Leu | Ile | Val | Ile | Cys | |
| | | | 20 | | | | | 25 | | | | | 30 | | | |

| CAC | TAT | TCT | CCT | GGT | GGA | AAT | ATG | GTT | GGA | GAG | GTG | ATA | TAC | CAG | CGA | 144 |
| His | Tyr | Ser | Pro | Gly | Gly | Asn | Met | Val | Gly | Glu | Val | Ile | Tyr | Gln | Arg | |
| | | 35 | | | | | 40 | | | | | 45 | | | | |

| GGT | AAT | CCG | TGT | AAA | GTC | GAC | AAA | GAT | TGC | TAT | ACG | AAA | AAA | TGT | TTA | 192 |
| Gly | Asn | Pro | Cys | Lys | Val | Asp | Lys | Asp | Cys | Tyr | Thr | Lys | Lys | Cys | Leu | |
| | 50 | | | | | 55 | | | | | 60 | | | | | |

| TCA | AAA | TCT | GGA | CTG | TGC | AGA | AAA | TG | AAAATTTTC | GCTTTCTTC | | | | | | 238 |
| Ser | Lys | Ser | Gly | Leu | Cys | Arg | Lys | | | | | | | | | |
| 65 | | | | 70 | | | | | | | | | | | | |

| ATTTAATTCT | TGGCTATATA | TCTCCTATAT | TAATTTTTCA | GCAAAAAAGC | TATAAAGAAA | 298 |
| TATTCATAAT | TAAATAAGAA | TATAGTAATT | AT | | | 330 |

( 2 ) INFORMATION FOR SEQ ID NO:7:

( i ) SEQUENCE CHARACTERISTICS:
        ( A ) LENGTH: 72 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Leu | His | Phe | Thr | Gln | Met | Ala | Trp | Gly | Lys | Thr | Tyr | Lys | Ile | Gly | Cys |
| 1 | | | | 5 | | | | | 10 | | | | | 15 | |
| Gly | Val | Ala | Thr | Gln | Cys | Asp | Gly | Gly | Arg | Thr | Leu | Ile | Val | Ile | Cys |
| | | | 20 | | | | | 25 | | | | | 30 | | |
| His | Tyr | Ser | Pro | Gly | Gly | Asn | Met | Val | Gly | Glu | Val | Ile | Tyr | Gln | Arg |
| | | 35 | | | | | 40 | | | | | 45 | | | |
| Gly | Asn | Pro | Cys | Lys | Val | Asp | Lys | Asp | Cys | Tyr | Thr | Lys | Lys | Cys | Leu |
| | 50 | | | | | 55 | | | | | 60 | | | | |
| Ser | Lys | Ser | Gly | Leu | Cys | Arg | Lys | | | | | | | | |
| 65 | | | | | 70 | | | | | | | | | | |

( 2 ) INFORMATION FOR SEQ ID NO:8:

( i ) SEQUENCE CHARACTERISTICS:
        ( A ) LENGTH: 216 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

| TTGCATTTCA | CACAAATGGC | TTGGGGTAAG | ACTTATAAAA | TTGGTTGCGG | TGTTGCAACA | 60 |
| CAATGTGATG | GTGGTAGAAC | ACTTATTGTT | ATTTGTCACT | ATTCTCCTGG | TGGAAATATG | 120 |
| GTTGGAGAGG | TGATATACCA | GCGAGGTAAT | CCGTGTAAAG | TCGACAAAGA | TTGCTATACG | 180 |
| AAAAAATGTT | TATCAAAATC | TGGACTGTGC | AGAAAA | | | 216 |

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO:9:

| CGTTGTTGTG | GATCCTTATG | AATGTGAAGG | AGG | 33 |

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO:10:

ATTAATCTGC AGTTACCCTT GTAAAATATC AAATATATG    39

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO:11:

CGCGGATCCT ATAAATATGA TACTTTTGGT TAT    33

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA primer ( x i ) SEQUENCE DESCRIPTION: SEQ ID NO:12:

GGCCTTAAGT TACCCTTGTA AAATAT    26

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule encoding a filatiid venom allergen antigen 5-like protein selected from the group consisting of: (a) a nucleic acid molecule encoding a protein having an amino acid sequence that is at least about 75% identical to SEQ ID NO:2, SEQ ID NO:5 or SEQ ID NO:7 and (b) a nucleic acid molecule encoding an epitope of a protein having at least about 75% identity to SEQ ID NO:2, SEQ ID NO:5 or SEQ ID NO: 7 wherein said protein or epitope encoded by the nucleic acid molecule of (a) and (b) are capable of eliciting an antibody response against the proteins having SEQ ID NO: 2 SEQ ID NO: 5 or SEQ ID NO:7.

2. An isolated nucleic acid molecule which is fully complementary to the nucleic acid molecule of claim 1.

3. The nucleic acid molecule of claim 1, wherein said filariid is selected from the group consisting of Dirofilaria and Onchocerca.

4. The nucleic acid molecule of claim 1, wherein said filariid is selected from the group consisting of *D. immitis* and *O. volvulus*.

5. The nucleic acid molecule of claim 1, wherein said nucleic acid molecule comprises a nucleic acid sequence that is at least about 75% identical to a nucleic acid sequence selected from the group consisting of: SEQ ID NO: 3 and SEQ ID NO: 8.

6. An isolated nucleic acid molecule which is fully complementary to the nucleic acid molecule of claim 5.

7. The nucleic acid molecule of claim 1, wherein said nucleic acid molecule comprises a nucleic acid molecule selected from the group consisting of: $nDIVA_{833}$, $nDiVA_{672}$, $nDiVA_{663}$, $nDiVA_{615}$, $nDiVA_{726}$, $nDiVA_{678}$, $nOvVA_{330}$ and $nOvVA_{216}$; or a nucleic acid molecule comprising a naturally occurring allelic variant of a nucleic acid molecule selected from the group consisting of $nDiVA_{833}$, $nDiVA_{672}$, $nDiVA_{663}$, $nDiVA_{615}$, $nDiVA_{726}$, $nDiVA_{678}$, $nOvVA_{330}$ and $nOvVA_{216}$.

8. The nucleic acid molecule of claim 1, wherein said nucleic acid molecule is selected from the group consisting of: a nucleic acid molecule comprising a nucleic acid sequence selected from the group consisting of SEQ ID NO: 1, SEQ ID NO: 3, SEQ ID NO: 4, SEQ ID NO: 6, SEQ ID NO: 8 and naturally occurring allelic variants thereof.

9. An isolated nucleic acid molecule which is fully complementary to the nucleic acid molecule of claim 8.

10. The nucleic acid molecule of claim 1, wherein said nucleic acid molecule encodes a protein comprising an amino of SEQ ID NO: 2, SEQ ID NO: 5, SEQ ID NO: 7 or naturally occurring allelic variants thereof.

11. A recombinant molecule comprising a nucleic acid molecule as set forth in claim 1 operatively linked to a transcription control sequence.

12. A recombinant virus comprising a recombinant molecule as set forth in claim 11.

13. A recombinant cell comprising a nucleic acid molecule as set forth in claim 1, said cell being capable of expressing said nucleic acid molecule.

* * * * *